United States Patent [19]

Rooney et al.

[11] 3,993,656

[45] Nov. 23, 1976

[54] 1,8-NAPHTHYRIDINE COMPOUNDS

[75] Inventors: Clarence Stanley Rooney, Beaconsfield; Haydn Windsor Richard Williams, Dollard des Ormeaux; Burton Kendall Wasson, Valois, all of Canada

[73] Assignee: Merck & Co., Inc., Rahway, N.J.

[22] Filed: Feb. 20, 1975

[21] Appl. No.: 551,565

Related U.S. Application Data

[63] Continuation-in-part of Ser. No. 525,235, Nov. 19, 1974, which is a continuation of Ser. No. 341,420, March 15, 1973, abandoned.

[52] U.S. Cl. ................ 260/296 N; 260/250 A; 260/250 BN; 260/256.4 R; 260/256.5 R; 260/294.8 C; 260/295 N; 424/250; 424/251; 424/256
[51] Int. Cl.$^2$.................................... C07D 471/04
[58] Field of Search ............... 260/294.8 C, 295 N, 260/296 N

[56] References Cited
OTHER PUBLICATIONS
Hawes, et al. J. Chem. Soc. (c), 1966, pp. 315–321.

*Primary Examiner*—Henry R. Jiles
*Assistant Examiner*—C. M. S. Jaisle
*Attorney, Agent, or Firm*—Edmunde D. Riedl; David L. Rose; J. Jerome Behan

[57] ABSTRACT

There is described 1,8-naphthyridin-2(1H)-one compounds with bronchodilating and hypotensive properties prepared by reaction of 2,6-diaminopyridine with an appropriate β-diketone providing a 2-aminonaphthyridine compound which upon treatment with nitrous acid is converted to the 2-oxo product. Alternatively, an appropriate β-diketone can be reacted with an alkyl alkoxycarbonylacetimidate, the alkyl 2-aminonicotinate thus formed converted to the hydrazide, which upon treatment with a sulfonyl halide forms the N-sulfonyl hydrazide derivative. This intermediate is reacted with an alkali metal carbonate to provide the 2-aminonicotinaldehyde which upon reaction with an ester of a substituted aliphatic carboxylic acid provides the desired product. In some cases the aminonicotinaldehyde is generated in situ in the presence of the ester thereby giving the desired product in one step from the N-sulfonyl hydrazide derivative.

6 Claims, No Drawings

1,8-NAPHTHYRIDINE COMPOUNDS

CROSS REFERENCE TO RELATED APPLICATIONS

This application is a continuation in-part of our co-pending application Ser. No. 525,235 filed Nov. 19, 1974 which in turn is a continuation of application Ser. No. 341,420 filed March 15, 1973 now abandoned.

This invention is concerned with 1,8-naphthyridin-2(1H)-one compounds and processes for their preparation.

The novel compounds of this invention have the general structural formula:

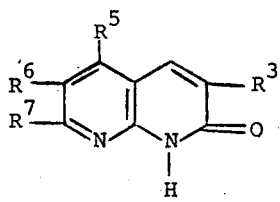

I wherein $R^5$ is phenyl or $R^7$, and $R^7$ is selected from hydrogen, lower alkyl having from 1 to 5 carbon atoms, halo substituted $C_{1-2}$— alkyl preferably trifluoromethyl and pentafluoroethyl, halophenyl (especially chloro- or fluorophenyl), benzyl, naphthyl, pyridyl and thienyl; $R^3$ represents hydrogen,

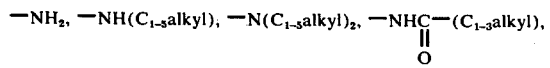

pyridyl, —$CO_2H$ or —$CO_2(C_{1-5}$—alkyl); $R^6$ represents hydrogen, amino,

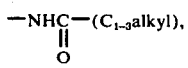

pyridyl, imidazolyl or other mono- or bicyclic N-heterocyclic groups such as a diazine (as pyrimidinyl, pyridazinyl, pyrazinyl), or an indolyl; and at least one of $R^3$ or $R^6$ is an N-containing substituent of the type hereinbefore defined provided that when $R^5$, $R^6$ and $R^7$ are all hydrogen, $R^3$ is other than —$CO_2(C_{1-5}$—alkyl) or pyridyl.

The products depicted above as 2-oxo compound are keto-enol tautomers illustrated by the formulae:

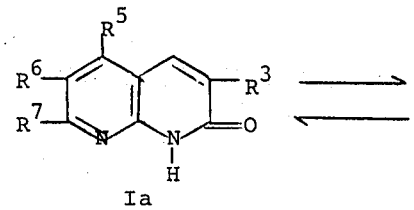

Ia

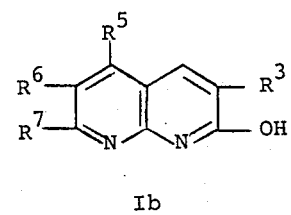

Ib

However as the keto form is considered the more stable tautomer, the products herein will be named and illustrated as 2-oxo compounds although those skilled in the art will realize that both tautomers may be present or any particular compound so named may exist as the enol or hydroxy tautomer and the following disclosure is to be interpreted to incorporate all tautomeric forms.

The naphthyridine compounds of this invention have been shown to increase the levels of 3',5'-cyclic adenosine monophosphate in vitro and have been found in animal studies to inhibit bronchial constriction induced by histamine and other constricting agents. The novel products are therefore useful as bronchodilating agents. As bronchodilating agents, the products of this invention have been found to have relatively low chronotropic effect as compared with known bronchodilating agents. Additionally the products possess hypotensive properties based on their activity as peripheral vasodilators and are therefore useful in treating hypertension. As the products are useful both in the free base form as well as in the form of acid-addition salts, both forms are within the purview of the invention.

The 1,8-naphthyridin-2(1H)-one products of this invention advantageously are prepared by one of the methods illustrated below:

METHOD I

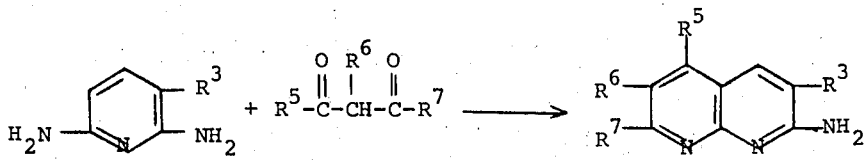

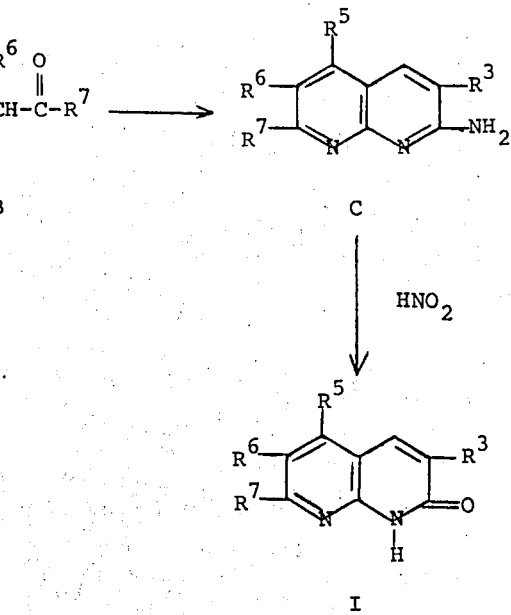

METHOD II

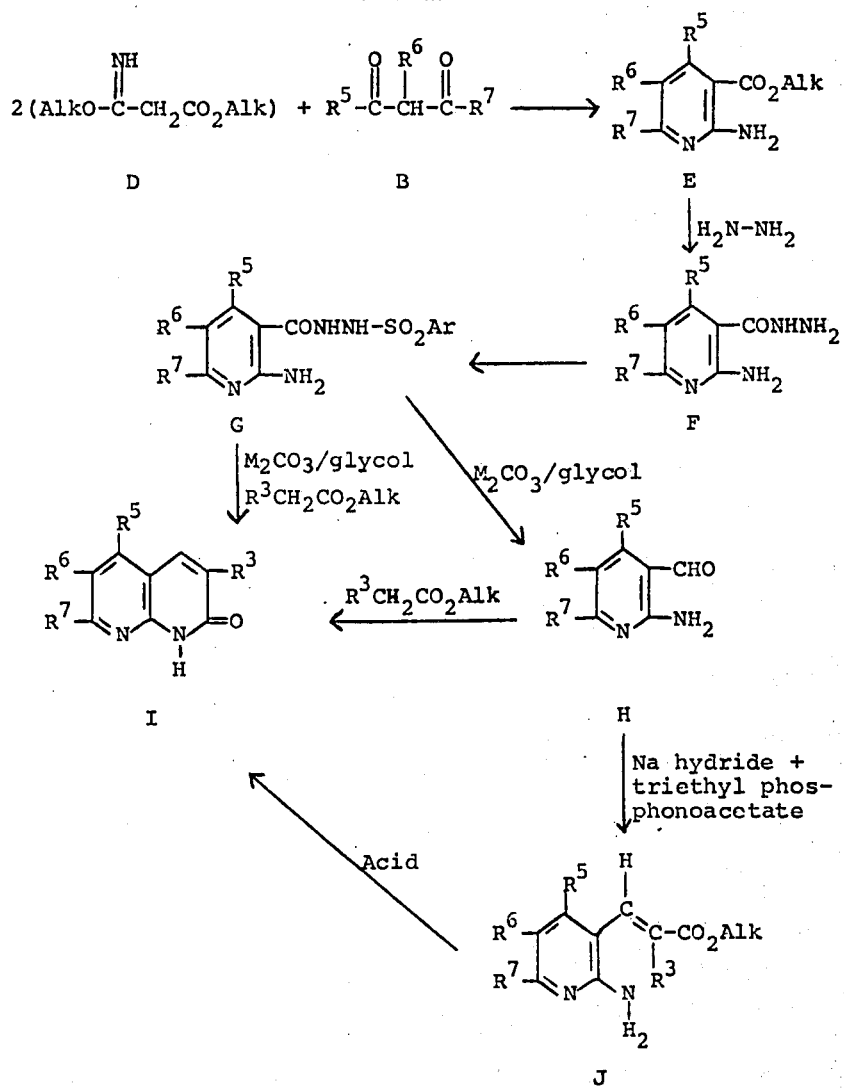

In Method I the reaction of the 2,6-diaminopyridine (A) with the appropriate $\beta$-diketone (B) provides the 2-amino-1,8-naphthyridine compounds (C) which upon reaction with nitrous acid gives the desired 2-oxo product, I. The first step of the reaction is facilitated by warming up to the boiling point although in practice lower temperatures, up to 90°–95° C., have been found to provide operable conditions.

The prior art procedure for converting 2-amino-1,8-naphthyridine compounds to the corresponding 2-oxo compound using dilute sulfuric acid and sodium nitrite was suitable for preparing most of the 2-oxo products, it proved inoperative for the compounds of this invention having a trifluoromethyl or pentafluoroethyl substituent attached to the naphthyridine nucleus. It was discovered, however, that conversion of the 2-amino to the 2-oxo group in these compounds (as well as all C intermediates) could be effected by use of trifluoroacetic acid or pentafluoropropionic acid and an alkali metal nitrite, suitably sodium or potassium nitrite, which provides the 2-oxo analog in good yield. Conversion takes place readily at ambient temperature. Slight warming would not, however, be contraindicated.

Method II comprises reaction of the appropriate $\beta$-diketone (B) with at least two equivalents of a lower alkyl lower alkoxycarbonylacetimidate (D). The particular alkyl or alkoxy group is not critical as they subsequently are removed in the preparation of the end products. The alkyl 2-aminonicotinate (E) formed is converted to the corresponding hydrazide (F) by heating with hydrazine. Reaction of the hydrazide with a sulfonyl halide such as toluenesulfonyl chloride, benzenesulfonyl chloride and the like gives the N-sulfonylhydrazide derivative (G). This intermediate can be reacted with an $R^3$-$CH_2CO_2$Alkyl in the presence of glycol, 1,4-diazabicyclo[2,2,2]octane and anhydrous alkali metal carbonate to provide the desired end product I. In some instances it may be more feasible to first convert the N-sulfonylhydrazide (G) to the corresponding aldehyde (H) by heating in the presence of glycol and an alkali metal carbonate ($M_2CO_3$), preferably sodium or potassium carbonate. The 2-aminonicotinaldehyde thus obtaind can be converted to the desired end product I by either of the following two procedures: (A) It can be reacted with an ester of the structure $R^3CH_2CO_2$Alkyl in the presence of piperidine or other conventional base catalyst, in a suitable solvent such as ethyl alcohol, advantageously with heating up to the reflux temperature of the reaction mixture or (B) it can be converted initially to the alkyl 3-(3-pyridyl)-acrylate (J) by combining with sodium hydride and triethyl phosphonoalkanoate at ambient temperature and then heating to reflux with concentrated mineral acid, suitably hydrochloric acid, to provide the desired end product I. When $R^3$ is amino, mono- or dialkylamino or acylamino, these compounds preferably are prepared from the 3-nitro-1,8-naphthyridin-2(1H)-one compounds I by conventional reduction procedures to give the 3-amino product which then can be alkylated or acylated by known methods.

The acid-addition salts of the 1,8-naphthyridin-2(1H)-one compounds obtained by any of the above procedures are prepared either by dissolving the free base in aqueous or aqueous-alcohol solution containing the appropriate acid and isolating the salt by evaporating the solution, or by reacting the free base and the selected acid in an organic solvent in which case the salt separates directly or can be obtained by concentration of the solution. The preferred salts are pharmacologically acceptable salts principally selected from mineral acids such as hydrochloric, hydrobromic, hydriodic, phosphoric, sulfamic and the like or organic acids such as acetic acid, citric acid, tartaric acid, methanesulfonic acid, benzenesulfonic acid, p-toluene sulfonic acid and the like. Although medicinally acceptable salts are preferred, all acid-addition salts are included within the scope of the invention since salt forms of various types can be formed for purpose of purification or identification and in some instances one salt can be used as an intermediate in preparing a medicinally acceptable salt by ion exchange procedures.

The following examples will provide details of the reaction conditions used in the various methods employed in preparing the compounds of this invention as well as illustrating the preparation of certain compounds falling within the scope of this invention.

EXAMPLE 1

6-Amino-5,7-dimethyl-1,8-naphthyridin-2(1H)-one

Step A:

Preparation of ethyl 2-amino-5-acetamido-4,6-dimethylnicotinate

A mixture of 3-acetamidopentan-2,4-dione (67.7 g., 0.431 mole) and ethyl ethoxycarbonylacetimidate (137.1 g., 0.862 mole) is heated at 100° C. overnight. On cooling, the reaction mixture solidifies partially, the solid is collected, slurried with isopropanol (40 ml.) and refiltered. The filter cake is washed with isopropanol (20 ml.) to give 45.3 g. (41.8%) of product, m.p. 168.5°–170° C. Recrystallization from chloroform provides product with m.p. 169°–170° C.

Analysis calculated for $C_{12}H_{17}N_3O_3$:
C, 57.36; H, 6.82; N, 16.72;
Found: C, 57.02; H, 6.90; N, 16.81.

Step B:

Preparation of 2-amino-5-acetamido-4,6-dimethylnicotinic acid hydrazide

A mixture of ethyl 2-amino-5-acetamido-4,6-dimethylnicotinate (45.3 g., 0.18 mole) and hydrazine hydrate (100 ml.) is heated in an oil bath with stirring at 120° C. for two hours. The mixture is cooled, the solid collected, and a second crop of solid obtained by evaporating the mother liquor to about half its initial volume. The combined solids melt at 293° C. (dec.), yield 38.1 g. (89%). Analytically pure compound is obtained by dissolving the solid in about six and one-half parts (volume by weight) of hot water and diluting the filtered solution with methanol. The purified product decomposed at about 309° C. with only partial melting.

Analysis calculated for $C_{10}H_{15}N_5O_2$:
C, 50.62; H, 6.37; N, 29.51;
Found: C, 50.84; H, 6.60; N, 29.60.

Step C:

Preparation of $N^1$-(2-amino-5-acetamido-4,6-dimethylnicotinoyl)-$N^2$-benzenesulfonyl hydrazine To a solution of 2-amino-5-acetamido-4,6-dimethylnicotinic acid hydrazide (34.4 g., 0.145 mole) in 1N sodium hydroxide solution (348 ml.) is added at ambient temperature and with vigorous stirring, benzenesulfonyl chloride (31.1 g., 0.16 mole) in one portion. After about three-quarters of an hour the acid chloride disappears; the maximum temperature attained by the reaction mixture, 36° C. The product is precipitated by pouring the reaction mixture into a stirred solution of acetic acid (8.3 ml.) in water (250 ml.). It is collected, slurried with water (150 ml.), refiltered and dried affording 49.52 g. (90%) of crude product, m.p. 216°–218° C. with gas evolution. Following purification by dissolving in hot (100° C.) dimethylformamide, filtering, and diluting with methanol (1 part) and water (3 parts) the product melts at 233°–234° C. (dec.).

Analysis calculated for $C_{16}H_{19}N_5O_4S$:
C, 50.92; H, 5.07; N, 18.56; S, 8.48;
Found: C, 51.24; H, 4.97; N, 18.76; S, 8.75.

Step D:

Preparation of 2-amino-5-acetamido-4,6-dimethylnicotinaldehyde

Ethylene glycol (80 ml.) is heated in an oil-bath at 170° C. until the internal temperature reaches 160° C. $N^1$-(2-amino-5-acetamido-4,6-dimethylnicotinoyl)-$N^2$-benzenesulfonyl hydrazine (8.0 g., 21.2 mmole) is added and the mixture stirred until the internal temperature returns to 160° C. Anhydrous sodium carbonate (5.6 g.) is added in one portion, heating is continued for 30 seconds and the reaction mixture cooled rapidly and poured into water (320 ml.). The product is isolated by continuous extraction with methylene chloride for about 24 hours to give 2.90 g. (66%) of crude product. Following purification by crystallization from ethanol the pure product melts at 270°–275° C. (dec.) with rapid heating.

Analysis calculated for $C_{10}H_{13}N_3O_2$:
C, 57.96; H, 6.32; N, 20.28; O, 15.44;
Found: C, 57.83; H, 6.46; N, 20.44; O, 15.26.

Step E:

Preparation of ethyl 3-(2-amino-5-acetamido-4,6-dimethylpyrid-3-yl)-acrylate To a suspension of sodium hydride (600 mg., 25 mmole) in dry glyme (40 ml.) is added a mixture of triethyl phosphonoacetate (5.6 g., 25 mmole) in dry glyme (10 ml.) dropwise with stirring and cooling in an ice-bath. Upon completion of the addition, the reaction mixture is stirred at ambient temperature until all sodium hydride reacts. Finely powdered 2-amino-5-acetamido-4,6-dimethylnicotinaldehyde (4.14 g., 20 mmole) is added in small portions over 30 minutes with stirring and cooling. The mixture then is stirred at ambient temperature for 72 hours whereupon the crude product is collected, washed with a small portion of 1:1 ethanol/acetonitrile mixture and dried yielding 4.93 g.

(90.5%) of product, m.p. 204°–205° C. Following recrystallization from acetonitrile pure product is obtained, m.p. 204.5°–205.5° C.

Analysis calculated for $C_{14}H_{19}N_3O_3$:
C, 60.63; H, 6.91; N, 15.15;
Found: C, 60.85; H, 6.90; N, 15.12.

Step F:

Preparation of 6-amino-5,7-dimethyl-1,8-naphthyridin-2(1H)-one

Ethyl 3-(2-amino-5-acetamido-4,6-dimethylpyrid-3-yl)-acrylate (2.48 g., 8.95 mmole) is heated under reflux in solution in 6N hydrochloric acid (24.8 ml.) for 6 days. The reaction mixture is filtered through a glass-fiber filter disc, the filtrate diluted slowly over a period of 15 minutes with ethanol (75 ml.) whereupon 1.043 g. (51.7%) of product in the form of the hydrochloride crystallizes from solution, m.p. 325° C. (dec.). A second crop raises the yield to 79%. Following recrystallization of the crude product from a mixture of dilute hydrochloric acid and isopropanol the purified product melts at 325° C. (dec.).

Analysis calculated for $C_{10}H_{11}N_3O.HCl$:
C, 53.22; H, 5.36; Cl, 15.71; N, 18.61;
Found: C, 53.28; H, 5.80; Cl, 15.79; N, 18.62.

EXAMPLE 2

3-Amino-5,7-dimethyl-1,8-naphthyridin-2(1H)-one Hydrochloride

Step A:

Preparation of 2-amino-4,6-dimethylnicotinic acid hydrazide

Ethyl 2-amino-4,6-dimethylnicotinate (42.5 g., 0.219 mole) and 85% hydrazine hydrate (62 g.) are stirred together at 120°–130° C. overnight. Excess hydrazine hydrate is removed by distillation under reduced pressure, the residue slurried with isopropanol and collected by filtration to yield 35.8 g. (90%) of product, m.p. 170°–175° C. Recrystallization from isopropanol provides product with m.p. 174°–176° C.

Analysis calculated for $C_8H_{12}N_4O$:
C, 53.32; H, 6.71; N, 31.09;
Found: C, 53.37; H, 6.87; N, 30.94.

Step B:

Preparation of $N^1$-(2-amino-4,6-dimethylnicotinoyl)-$N^2$-benzenesulfonyl hydrazine A solution of 2-amino-4,6-dimethylnicotinic acid hydrazide (127 g., 0.69 mole) in 1N sodium hydroxide solution (1.655 l.) is treated with benzenesulfonyl chloride (134 g., 0.76 mole) and the mixtutre stirred at ambient temperature until a clear yellow solution forms. The reaction mixture is poured into a stirred solution of acetic acid (41.5 ml.) in water (1.73 l.) and the pH of the mixture adjusted to about 6.5 by the addition of more acetic acid. The solid material is collected, washed with water and dried yielding 203 g. (92%) of product, m.p. 162°–166° C. Following recrystallization from isopropanol the product obtained contains 1 mole of isopropanol of crystallization and partially melts at about 105° C., finally melting at 165°–167° C.

The same product is obtained by carrying out the reaction with benzenesulfonyl chloride in pyridine.

Analysis calculated for $C_{14}H_{16}N_4O_3S.C_3H_8O$:
C, 53.67; H, 6.36; N, 14.72; S, 8.42;
Found: C, 53.50; H, 6.16; N, 15.11; S, 8.52.

Step C:

Preparation of 2-amino-4,6-dimethylnicotinaldehyde $N^1$-(2-amino-4,6-dimethylnicotinoyl)-$N^2$-benzenesulfonyl hydrazine isopropanolate (62.0 g., 0.163 mole) is divided into two portions. To each portion, ethylene glycol (300 ml.) is added and the mixture heated to 160° C. prior to the addition of anhydrous sodium carbonate (30 g.) in one portion with vigorous stirring. The mixture is allowed to cool and then is poured into water. The two runs are combined and the product isolated by extraction with chloroform. Following recrystallization from carbon tetrachloride the product melts at 152°–158° C. Further recrystallization from the same solvent raises the melting point to 162°–166° C.

Analysis calculated for $C_8H_{10}N_2O$:
C, 63.98; H, 6.71; N, 18.65;
Found: C, 63.69; H, 6.69; N, 18.54.

Step D:

Preparation of 3-nitro-5,7-dimethyl-1,8-naphthyridin-2(1H)-one

A mixture of 2-amino-4,6-dimethylnicotinaldehyde (2.40 g., 16 mmole), ethyl nitroacetate (5.12 g., 32 mmole), piperidine (336 mg., 4 mmole) and ethanol (4 ml.) is heated under reflux with stirring for an hour. The mixture then is cooled, treated with petroleum ether, the solid removed by filtration and recrystallized from methanol yielding 1.55 g. (44%) of product, m.p. 270°–272° C. (dec.). Following recrystallization from the same solvent the product melts at 272°–274° C. (dec.).

Analysis calculated for $C_{10}H_9N_3O_3$:
C, 54.79; H, 4.14; N, 19.17;
Found: C, 54.68; H, 4.26; N, 19.11.

Step E:

Preparation of 3-amino-5,7-dimethyl-1,8-naphthyridin-2(1H)-one Hydrochloride 3-Nitro-5,7-dimethyl-1,8-naphthyridin-2(1H)-one (6.0 g., 27.4 mmole) is suspended in acetic acid (250 ml.) and hydrogenated at about 50 lbs./sq. in. in the presence of platinum oxide (250 mg.). When the theoretical amount, or a slight excess, of hydrogen has been taken up, the catalyst is removed by filtration, the filtrate boiled with charcoal and refiltered. The solvent is removed by evaporation under vacuum and the residue converted to a hydrochloride salt by treatment with ethanolic hydrogen chloride solution. Recrystallization of the product from methanol containing charcoal provides 6.30 g. (theoretical) yield of product which following further recrystallization from methanol melts at 306°–309° C.

Analysis calculated for $C_{10}H_{11}N_3O.HCl$:
C, 53.22; H, 5.36; Cl, 15.71; N, 18.61;
Found: C, 53.18; H, 5.58; Cl, 15.45; N, 18.82.

The products identified in Table I are prepared following the method of Example 1, Step A, replacing the 3-acetamidopentan-2,4-dione employed therein by an equivalent quantity of the β-diketone identified in the table. By substituting the nicotinate thus obtained for the one employed in Example 2, Step A, and then following the procedures described in Example 2, Steps A through E, there is obtained the 3-amino-5-$R^5$-7-$R^7$-

1,8-naphthyridin-2(1H)-one products having the $R^5$ and $R^7$ substituents identified in Table I:

TABLE I

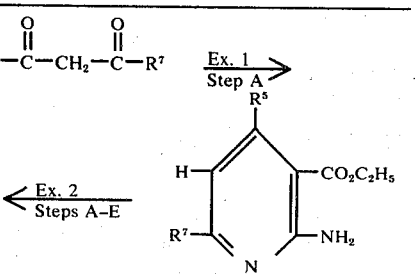

| Ex. No. | $R^5$ | $R^7$ |
|---|---|---|
| 3 | p-fluorophenyl | p-fluorophenyl |
| 4 | isopropyl | isopropyl |
| 5 | 2-naphthyl | 2-naphthyl |
| 6 | ethyl | ethyl |
| 7 | ethyl | methyl |
| 8 | isopropyl | ethyl |
| 9 | n-propyl | n-propyl |
| 10 | phenyl | methyl |
| 11 | benzyl | methyl |
| 12 | t-butyl | trifluoromethyl |
| 13 | ethyl | trifluoromethyl |
| 14 | isobutyl | trifluoromethyl |
| 15 | isopropyl | trifluoromethyl |
| 16 | 2-naphthyl | trifluoromethyl |
| 17 | isopentyl | trifluoromethyl |
| 18 | phenyl | trifluoromethyl |
| 19 | 3-pyridyl | trifluoromethyl |
| 20 | 2-thienyl | trifluoromethyl |

EXAMPLE 21
3-Acetamido-5,7-dimethyl-1,8-naphthyridin-2(1H)-one

3-Nitro-5,7-dimethyl-1,8-naphthyridin-2(1H)-one (660 mg., 3 mmole), prepared as described in Example 2, Steps A-D, in acetic anhydride (25 ml.) is hydrogenated at about 50 lbs./sq. in. in the presence of platinum oxide (30 mg.). Hydrogenation is complete in about one and a half hours. Acetic acid is added to dissolve the white solid suspended in the reaction mixture and the solution heated until the solid is completely dissolved. The catalyst is filtered off, the filtrate treated with charcoal and refiltered hot. Evaporation of the filtrate afforded 400 mg. of product which after recrystallization from ethyl acetate melted at 244°–246° C. after sintering at 224° C. The solid is redissolved in hot ethyl acetate, a small quantity of anhydrous potassium carbonate is added to remove acetic acid, the mixture filtered and cooled yielding 220 mg. of product, m.p. 248°–251° C.

Analysis calculated for $C_{12}H_{13}N_3O_2$:
C, 62.33; H, 5.67; N, 18.17;
Found: C, 62.26; H, 6.00; N, 18.03.

By sequentially replacing the 3-nitro-5,7-dimethyl-1,8-naphthyridin-2(1H)-one employed in Example 21 by an equivalent quantity of the 3-nitro intermediate of the products of Examples 3–20 (prepared by Example 1, Step A, and Example 2, Steps A-D procedures) there is obtained in each instance the 3-acetamido derivatives of the products of Examples 3–20.

EXAMPLE 22
3-Isopropylamino-5,7-dimethyl-1,8-naphthyridin-2(1H)-one Hydrochloride 3-Amino-5,7-dimethyl-1,8-naphthyridin-2(1H)-one (378 mg., 2 mmole) obtained as described in Example 2, is dissolved in acetic acid (50 ml.) containing acetone (1.2 ml.) and the mixture hydrogenated at about 50 lbs./sq. in. in the presence of platinum oxide (55 mg.). The reaction mixture is filtered, the filtrate evaporated to dryness and the residue treated with ammonium hydroxide to provide 340 mg. (74%) of product. The product is converted to the hydrogen chloride salt by treatment with ethanolic hydrogen chloride solution and the product recrystallized from isopropanol yielding 240 mg. (45%) of product as the hydrochloride salt, m.p. 238°–240° C. after sintering at 205° C.

Analysis calculated for $C_{13}H_{17}N_3O.HCl$:
C, 58.31; H, 6.78; Cl, 13.24; N, 15.69;
Found: C, 57.98; H, 6.88; Cl, 12.99; N, 16.04.

By sequentially replacing the 3-amino-5,7-dimethyl-1,8-naphthyridin-2(1H)-one employed in Example 22 by an equivalent quantity of the products of Examples 3–20 and following the procedure of Example 22, there is obtained in each instance the 3-isopropylamino derivative of the products of Examples 3–20.

EXAMPLE 23
3-Dimethylamino-5,7-dimethyl-1,8-naphthyridin-2(1H)-one Hydrochloride 3-Nitro-5,7-dimethyl-1,8-naphthyridin-2(1H)-one (438 mg., 2 mmole), obtained as described in Example 2, Steps A-D, is suspended in a mixture of ethanol (5 ml.) and acetic acid (25 ml.). Formaldehyde solution (0.9 ml., 10 mmole) is added and the mixture hydrogenated at about 50 lbs./sq. in. in the presence of 10% palladium on charcoal (300 mg.) until uptake of hydrogen ceases. The solution is filtered, evaporated to dryness and the residue dissolved in a small quantity of methanol and a slight excess of ethanolic hydrogen chloride is added. Dry ether precipitates the hydrochloride of the product yielding 400 mg. (79%), m.p. 230°–235° C. Following recrystallization from isopropanol the monohydrochloride of the product melts at 232°–235° C.

Analysis calculated for $C_{12}H_{15}N_3O \cdot HCl$:
C, 56.80; H, 6.36; Cl, 16.56; N, 13.97;
Found: C, 57.24; H, 6.43; Cl, 16.12; N, 13.71.

By sequentially replacing the 3-nitro-5,7-dimethyl-1,8-naphthyridin-2(1H)-one employed in Example 23 by an equivalent quantity of the 3-nitro intermediate of Examples 3–20 products, and following the procedure of Example 23 there is obtained in each instance the 3-dimethylamino derivative of the products of Examples 3–20.

EXAMPLE 24

6-(4-Pyridyl)-1,8-naphthyridin-2(1H)-one Hydrochloride

Step A:

Preparation of 2-amino-6-(4-pyridyl)-1,8-naphthyridine Dihydrochloride

A mixture of 2,6-diaminopyridine (4.76 mmole), 2-(4-pyridyl)-propan-1,3-dione (4.80 mmole) and 85% phosphoric acid (50 ml.) is stirred for six hours in an oil-bath at 90°–95° C., then left overnight at ambient temperature. The mixture is poured into ice water and neutralized with ammonium hydroxide to pH 7, the solid collected, washed with water and dried to give a 57% yield of product which after crystallization as a dihydrochloride salt from methanol does not melt up to 350° C.

Analysis calculated for $C_{13}H_{12}N_4Cl_2$: C, 52.89; H, 4.09; N, 18.98; Cl, 24.02;
Found: C, 53.01; H, 4.34; N, 18.85; Cl, 24.06.

Step B: Preparation of 6-(4-pyridyl)-1,8-naphthyridin-2(1H)-one Hydrochloride

2-Amino-6-(4-pyridyl)-1,8-naphthyridine (16.95 mmole) is dissolved in trifluoroacetic acid (50 ml.). To the stirred, cooled (ice-bath), solution is added finely powdered sodium nitrite (3.0 g., 43.5 mmole) in small portions. Stirring is continued at ambient temperature for one hour, the mixture then poured into water containing crushed ice (circa 500 ml.), the solid product removed by filtration and dried in an oven at 50° C. providing 1.7 g. (39%) yield. The product in the form of the hydrochloride salt melts above 350° C. after crystallization from methanol.

Analysis calculated for $C_{13}H_9N_3O \cdot HCl$:
C, 60.12; H, 3.88; Cl, 13.65; N, 16.18;
Found: C, 60.29; H, 4.28; Cl, 13.87; N, 16.32.

EXAMPLE 25

3-(4-Pyridyl)-5,7-dimethyl-1,8-naphthyridin-2(1H)-one Hydrochloride

By following the procedure of Example 2, Step D, with the exception that ethyl nitroacetate is replaced by an equivalent quantity of methyl 4-pyridyl acetate and reflux with stirring is continued for 48 hours there is obtained a 55% yield of product which when recrystallized as the hydrochloride salt from methanol melts at 306°–310° C.

Analysis calculated for $C_{15}H_{13}N_3O \cdot HCl$:
C, 62.61; H, 4.90; Cl, 12.32; N, 14.60;
Found: C, 62.30; H, 4.50; Cl, 12.08; N, 14.72.

EXAMPLE 26

3-(3-Pyridyl)-5,7-dimethyl-1,8-naphthyridin-2(1H)-one Hydrochloride

By following the procedure of Example 2, Step D, with the exception that ethyl 3-pyridyl acetate is employed in place of ethyl nitroacetate and refluxing is continued for 72 hours there is obtained a 35% yield of product which after purification as the hydrochloride salt by recrysallization from a mixture of methanol and diethyl ether melts at 297°–301° C.

Analysis calculated for $C_{15}H_{13}N_3O \cdot HCl$:
C, 62.61; H, 4.90; Cl, 12.32; N, 14.60;
Found: C, 62.43; H, 4.88; Cl, 12.45; N, 14.76.

EXAMPLE 27

3-(2-Pyridyl)-5,7-dimethyl-1,8-naphthyridin-2(1H)-one Hydrochloride

By following the procedure of Example 2, Step D, but employing ethyl 2-pyridyl acetate in place of the nitroacetate there employed and continuing heating at reflux for 72 hours there is obtained a 37% yield of product which when purified as the hydrochloride salt by recrystallization from methanol melts at 270°–273° C.

Analysis calculated for $C_{15}H_{13}N_3O \cdot HCl$:
C, 62.61; H, 4.90; Cl, 12.32; N, 14.60;
Found: C, 62.38; H, 5.07; Cl, 12.16; N, 14.53.

EXAMPLE 28

Ethyl 6-acetamido-5,7-dimethyl-1,8-naphthyridin-2(1H)-one-3-carboxylate

By replacing in Example 2, Step D, the 2-amino-4,6-dimethylnicotinaldehyde and the ethyl nitroacetate by equivalent quantities of 2-amino-5-acetamido-4,6-dimethylnicotinaldehyde (prepared as described in Example 1, Step D) and diethyl malonate, respectively, and following substantially the same procedure described in Step D of Example 2 there is obtained after refluxing for 17 hours an 87% yield of product which after recrystallization from a mixture of chloroform and carbon tetrachloride separates with one mole of water of crystallization, m.p. 231°–232° C.

Analysis calculated for $C_{15}H_{17}N_3O_4 \cdot H_2O$:
C, 56.02; H, 5.63; N, 13.31;
Found: C, 56.06; H, 5.93; N, 13.08.

EXAMPLE 29

6-Acetamido-5,7-dimethyl-1,8-naphthyridin-2(1H)-one-3-carboxylic acid

Ethyl 6-acetamido-5,7-dimethyl-1,8-naphthyridin-2(1H)-one-3-carboxylate (321 mg., 1 mmole), prepared as described in Example 28, is dissolved in water (2 ml.) to which has been added 40% w/w potassium hydroxide solution (0.28 ml.) and the clear solution heated on a steam bath for 2 hours. The solution is cooled and acidified to pH 5.5 with dilute acetic acid giving initially a gelatinous precipitate which becomes denser and more crystalline on standing at ambient temperature. The product is collected, washed with water and dried yielding 195 mg. (66%) of product, m.p. 305° C. (dec.). The product is purified by dissolving in dilute ammonium hydroxide solution, treating with charcoal and reprecipitating with acetic acid with no change in melting point.

Analysis calculated for $C_{13}H_{13}N_3O_4$:

C, 56.72; H, 4.76; N, 15.27;
Found: C, 56.53; H, 4.72; N, 15.14.

EXAMPLE 29

3-(4-Pyridyl)-5,7-di(trifluoromethyl)-1,8-naphthyridin-2(1H)-one

Step A:

Preparation of ethyl 2-amino-4,6-di(trifluoromethyl)-nicotinate 1,1,1,5,5,5-Hexafluoroacetylacetone (39.0 g., 0.188 mole) is added slowly over 15 minutes to ethyl ethoxycarbonylacetimidate (59.6 g., 0.375 mole) with stirring and cooling in an ice-bath. The mixture is stirred for 15 minutes at ambient temperature and then for 20 hours in an oil-bath at 105°–110° C. The contents of the flask are distilled and the fraction having b.p. 65°–88°10.05 mm. is collected. The fraction of product that solidifies in the condensor and still-head can be scraped out and added to the semi-solid product in the receiver. The solid product is freed from the oily material by filtration, washed on the filter with a little cold alcohol and collected yielding 10.44 g. (18.6%) of product, m.p. 84°–86° C. Following purification by recrystallization from a 2:1 mixture of methanol and water followed by sublimation at 45° C./0.005 mm., product having m.p. 87°–88° C. is obtained.

Analysis calculated for $C_{10}H_8F_6N_2O_2$:
C, 39.75; H, 2.67; F, 37.72; N, 9.27;
Found: C, 39.61; H, 2.96; F, 37.80; N, 9.66.

Step B:

Preparation of 2-amino-4,6-di(trifluoromethyl)-nicotinic acid hydrazide

A mixture of ethyl 2-amino-4,6-di(trifluoromethyl)-nicotinate (2.55 g., 8.45 mmole), 85% hydrazine hydrate (5 ml.) and isopropanol (5 ml.) is stirred in an oil-bath at 110° C. for 3 hours. On cooling, the dark red solution deposits colorless crystals which are filtered off and washed with a little isopropanol. A second crop of solid is obtained by evaporation of the mother liquors giving a total yield of 1.45 g. (59.6%) of product, m.p. 240°–243° C. (dec.). Upon recrystallization from isopropanol (25 ml.) there is obtained 1.05 g. (42.8%) of product, m.p. 244°–245° C. (dec.).

Analysis calculated for $C_8H_6F_6N_4O$:
C, 33.35; H, 2.10; F, 39.56; N, 19.44;
Found: C, 33.27; H, 2.20; F, 39.48; N, 19.50.

Step C:

Preparation of $N^1$-[2-amino-4,6-di(trifluoromethyl)nicotinoyl]-$N^2$-benzenesulfonyl hydrazine 2-Amino-4,6-di(trifluoromethyl)-nicotinic acid hydrazide (4.35 g., 15.1 mmole) is stirred in 1N sodium hydroxide solution (36.3 ml.) untila clear solution is obtained. Benzenesulfonyl chloride (2.94 g., 16.6 mmole) is added in one portion and the mixture stirred rapidly until solution is complete. On pouring this solution into a stirred solution of acetic acid (0.9 g., 15 mmole) in water (40 ml.), a fine precipitate is formed. The pH of the suspension is adjusted to circa 6.5 with acetic acid and the product collected, washed with water and dried giving 6.52 g. (theoretical) of product sintering at circa 230° C., m.p. 235°–238° C. (dec.). The product is obtained pure by precipitation from a filtered solution of the crude product in ethyl acetate (4 parts volume by weight) by addition of chloroform (10 parts volume by weight) providing product with m.p. 243°–245° C. (dec.).

Analysis calculated for $C_{14}H_{10}F_6N_4O_3S$:
C, 39.26; H, 2.35; N, 13.08; S, 7.49;
Found: C, 39.72; H, 2.78; N, 13.20; S, 7.55.

Step D:

Preparation of 3-(4-pyridyl)-5,7-di(trifluoromethyl)-1,8-naphthyridin-2(1H)-one Glycol (30 ml.) is heated in a oil-bath at 175° C. $N^1$-[2-amino-4,6-di(trifluoromethyl)-nicotinoyl]-$N^2$-benzenesulfonyl hydrazine (1.28 g., 3 mmole) is added followed immediately by a solution of methyl 4-pyridyl acetate (453 mg., 3 mmole) and 1,4-diazabicyclo[2,2,2]octane (336 mg., 3 mmole) in ethylene glycol (6 ml.). The mixture is stirred vigorously until the temperature reaches 160° C. whereupon anhydrous sodium carbonate (900 mg.) is added. Heating in the oil-bath is continued for one minute and the reaction mixture then is allowed to cool and is then poured into water (200 ml.). Precipitation of the product is initiated by the addition of a single drop of acetic acid. A fine ochre colored solid is collected after it crystallizes overnight giving 639 mg. of product, m.p. 235°–236° C. Neutralization of the mother liquors to pH 7 with acetic acid provides an additional 51 mg. of product, m.p. circa 250°–270° C. Purification of the combined crude material by soxhlet extraction with acetonitrile gives 328 mg. (30%) of product., m.p. 282°–285° C. with some decomposition.

Analysis calculated for $C_{15}H_7F_6N_3O$:
C, 50.15; H, 1.96; N, 11.69;
Found: C, 49.61; H, 2.19; N, 11.87.

EXAMPLE 30

3-(2-Pyridyl)-5,7-di(trifluoromethyl)-1,8-naphthyridin-2(1H)-one

By replacing the methyl 4-pyridyl acetate employed in Example 12, Step D, by an equivalent quantity of ethyl 2-pyridyl acetate and following substantially the same procedure described in Step D of Example 12 there is obtained a 31% yield of product which after crystallization from acetonitrile melts at 298°–300° C.

Analysis calculated for $C_{15}H_7F_6N_3O$:
C, 50.15; H, 1.96; N, 11.69;
Found: C, 49.89; H, 2.15; N, 11.48.

EXAMPLE 31

6-(2-Imidazolyl)-1,8-naphthyridin-2(1H)-one

Step A:

Preparation of [3-(Dimethylamino)-2-(imidazol-2-yl)-allylidene]-dimethylammonium hexafluorophosphate The Vilsmeier Haack reagent is prepared using 140 ml. (1.8 mole) of dimethylformamide and 500 ml. of 3N phosgene in chloroform. 2-Methylimidazole (30.8 g., 0.375 mole) is added in portions over one hour maintaining the temperature at or below 10° C. and the mixture is then stirred overnight at ambient temperature. The reaction mixture is poured onto ice (490 g.), shaken and separated. The chloroform solution is extracted with water (35 ml.) and the combined aqueous solutions treated with sodium hexafluorophosphate (63.0 g., 0.375 mole). After filtering, the filtrate is cooled in an ice-bath while sodium carbonate anhydrate (139 g., 1.313 mole) is added in small portions. The crystalline precipitate obtained weighs 50.70 g. (39%) and melts at 185°–187° C. Recrystallization of the crude product from water (5 parts volume by weight) gives purified product melting at 191°–192° C. in the form of colorless crystals.

Analysis calculated for $C_{10}H_{17}N_4 \cdot PF_6 \cdot 1/2H_2O$:
C, 34.51; H, 4.97; N, 16.15;
Found: C, 34.59; H, 5.22; N, 16.14.

Step B:

Preparation of 2-(2-imidazolyl)-propan-1,3-dione

A solution of the product obtained in Step A (23.6 g., 0.068 mole) in 2N sodium hydroxide (70 ml.) is maintained at 65°–70° C. for one hour. 6N hydrochloric acid then is added dropwise to the hot solution with stirring and when the pH is 7.0–7.5 the mixture is cooled to 5° C. to give 7.88 g. (81.5%) of product. Following purification by suspending the crude material in hot water (5 parts volume by weight) and adding solid sodium carbonate to effect solution, filtering and then reprecipitating the product by neutralization with acetic acid the product melts at 278°–280° C. (dec.).

Analysis calculated for $C_6H_6N_2O_2$:
C, 52.17; H, 4.38; N, 20.28;
Found: C, 51.96; H, 4.62; N, 20.10.

Step C:

Preparation of 2-amino-6-(2-imidazolyl)-1,8-naphthyridine

By replacing the 2-(4-pyridyl)-propan-1,3-dione employed in Example 24, Step A, by an equivalent quantity of 2-(2-imidazolyl)-propan-1,3-dione and following substantially the same procedure described in Step A of Example 24 there is obtained a 70% yield of product which after recrystallization from water melts at 340° C. (dec.).

Step D:

Preparation of 6-(2-imidazolyl)-1,8-naphthyridin-2(1H)-one

To a mixture of 2-amino-6-(2-imidazolyl)-1,8-naphthyridine (211 mg., 1 mmole) in 40% sulphuric acid (2.5 ml.) at 5° C. is added with stirring sodium nitrite (69 mg., 1 mmole). The solution is allowed to warm to room temperature and then heated at 50° C. for 4 hours. The reaction mixture then is cooled to 5° C. and more sodium nitrite (40 mg., 0.57 mmole) added to ensure reaction goes to completion. The mixture then is heated at 50° C. for two hours, cooled to room temperature, diluted with water and neutralized with ammonium hydroxide affording 140 mg. of solid. The product is purified by dissolving in dilute acetic acid (5 ml.), treating the solution with charcoal, and neutralizing the filtered solution with a few drops of ammonium hydroxide. The product (100 mg., 47%) did not melt below 350° C.

Analysis calculated for $C_{11}H_8N_4O$:
C, 62.25; H, 3.80; N, 26.40;
Found: C, 62.40; H, 3.84; N, 26.41.

EXAMPLE 32

3-Amino-5,7-di(pentafluoroethyl)-1,8-naphthyridin-2(1H)-one

Step A:

Preparation of 1,1,1,2,2,6,6,7,7,7-Decafluoroheptan-3,5-dione

To a stirred suspension of potassium t-butoxide (44.8 g., 0.4 mole) in dry ether (400 ml.) is added ethyl pentafluoropropionate (76.8 g., 0.4 mole) over a period of about 15 minutes. Most of the solid dissolves. A solution of pentafluoroethyl methyl ketone (64.8 g., 0.4 mole) in dry ether (60 ml.) is added slowly, and after stirring the mixture for 2 hours at room temperature, it is allowed to stand overnight. A solution of glacial acetic acid (27.2 ml.) in water (120 ml.) is added with stirring and external cooling (ice-bath). Then a warm solution of copper acetate (56.0 g., 0.28 mole) in water (532 ml.) is added slowly with stirring and cooling. The ether is distilled off, and the copper salt of the product is collected by filtration, washed with water, drained thoroughly, and then washed with petroleum ether. The copper derivative is suspended in ether (200 ml.) and decomposed by treatment with 15% sulphuric acid (450 ml.). The aqueous layer is separated and extracted with more ether (3 × 50 ml.). The combined ethereal extract is dried, first over anhydrous sodium sulphate and then over anhydrous calcium sulphate. Evaporation of the ether gives the product which is purified by fractionational distillation at atmospheric pressure.

Step B:

Preparation of ethyl 2-amino-4,6-di(pentafluoroethyl)nicotinate

By replacing the 3-acetamidopentan-2,4-dione employed in Example 1, Step A, by an equivalent quantity of 1,1,1,2,2,6,6,7,7,7-decafluoroheptan-3,5-dione and following the procedure of Step A of Example 1, there is obtained ethyl 2-amino-4,6-di(pentafluoroethyl)-nicotinate.

Step C:

Preparation of 3-amino-5,7-di(pentafluoroethyl)-1,3-naphthyridin-2(1H)-one

This product is prepared by replacing the nicotinate employed in Step A of Example 2 by an equivalent quantity of ethyl 2-amino-4,6-di(pentafluoroethyl)-nicotinate and then following the procedure of Steps A through E of Example 2.

EXAMPLE 33

3-Amino-5-methyl-7-pentafluoroethyl-1,8-naphthyridin-2(1H)-one

Step A:

Preparation of (1) ethyl 2-amino-4-pentafluoro-6-methylnicotinate and (2) ethyl 2-amino-4-methyl-6-pentafluoroethylnicotinate Ethoxycarbonylacetimidate (7.1 g., 28.3 mmole) and 5,5,6,6,6-pentafluorohexan-2,4-dione (2.86 g. 14 mmole) were heated together at 100° C. overnight. Distillation of the mixture at ca. 0.03 mm gave 4.75 g. of distillate, b.p. 71°–102° C. Chromatography of the distillage on silica gel using methylene chloride as solvent afforded the two isomers, m.p.'s 98°–100° C. and 77°–81° C.

Step B:

Preparation of 3-amino-5-pentafluoroethyl-7-methyl-1,8-naphthyridin-2(1H)-one The fraction containing ethyl 2-amino-4-pentafluoroethyl-6-methylnicotinate was reacted with hydrazine hydrate by substantially the same procedure described in Example 2, Step A, followed by the methods of Steps B-E to provide 3-amino-5-pentafluoroethyl-7-methyl-1,8-naphthyridin-2(1H)-one.

Step C:

Preparation of 3-amino-5-methyl-7-pentafluoroethyl-1,8-naphthyridin-2(1H)-one This product is also prepared by the process described in Example 2, Steps A-E by substituting an equivalent quantity of ethyl 2-amino-4-methyl-6-pentafluoroethylnicotinate for the nicotinate employed in Step A of Example 2.

EXAMPLE 34

6-(3-Indolyl)-1,8-naphthyridin-2(1H)-one Hydrochloride

Step A:

Preparation of [3-(Dimethylamino)-2-(1-formylindol-3-yl)allylidene]-dimethylammonium Tetrafluoroborate To dry N,N-dimethylformamide (132 g., 1.8 mole) cooled in an ice-bath is added phosphoryl chloride (55.2 g., 0.36 mole) dropwise with stirring. To the cold mixture is added indole-3-acetic acid (21 g., 0.12 mole), and the mixture is heated slowly to 90° C. and maintained at that temperature for 3 hours. Excess dimethylformamide is distilled off at the water-pump and the residue is quenched with ice (100 g.). The aqueous solution is treated with charcoal and filtered. Addition of a solution of sodium tetrafluoroborate (14.5 g., 0.132 mole) in a small volume of water (ca. 30 ml.) precipitates the crude trimethinium salt, which is crystallized from 3:1 mixture of ethanol/methanol (400 ml.) to afford 16 g. of black solid. This solid is recrystallized three times from methanol with treatment with charcoal to give pure product crystallizing in colorless platelets, m.p. 202°–204° C., 8.86 g. (20.6%).

Analysis calculated for $C_{16}H_{20}BF_3N_3O$:
C, 53.80; H, 5.64; N, 11.98; F, 21.27;
Found: C, 53.00; H, 5.83; N, 11.76; F, 20.91.

Step B:

Preparation of 3-Dimethylamino-2-(3-indolyl)acrolein

The trimethinium salt obtained in Step A (990 mg., 3 mmole) is stirred with 1N sodium hydroxide solution at 70° C. for one hour. The solid is filtered off and washed with water yielding 564 mg. (88%) of compound, m.p. 188°–190° C. (dec.). Recrystallization of the crude product from alcohol (11.5 ml.) affords the pure compound crystallizing in cream-colored prisms, m.p. 191°–192° C. with slight darkening.

Analysis calculated for $C_{13}H_{14}N_2O$:
C, 72.87; H, 6.59; N, 13.08;
Found: C, 72.41; H, 6.84; N, 12.68.

Step C:

Preparation of 3-Indolylmalondialdehyde

A suspension of the enamino aldehyde from Step B (1.07 g., 5 mmole) in alcohol (15 ml.) is treated with 10N sodium hydroxide solution (0.60 ml.) and the mixture is heated at reflux under nitrogen for 9 hours. The alcohol is distilled off under reduced pressure and the residue is slurried with ca. 10 ml. of 1N sodium hydroxide solution and filtered. Methanol (5 ml.) is added to the filtrate and the pH of the mixture is adjusted to ca. 3.5 by dropwise addition of 6N hydrochloric acid. The product is collected and washed with water affording 565 mg. (61%) of crude product, m.p. 166°–167° C. (dec.). Recrystallization of this solid from nitromethane (5.5 ml.) to which one drop of water is added gives the pure compound, m.p. 170.5°–171.5° C. with slight darkening above 165° C.

Analysis calculated for $C_{11}H_9NO_2 \cdot 1/3H_2O$:
C, 68.38; H, 5.04; N, 7.25;
Found: C, 68.18; H, 4.95; N, 7.49.

Step D:

Preparation of 6-(3-Indolyl)-1,8-naphthyridin-2(1H)-one hydrochloride

This product is prepared by replacing the 2-(4-pyridyl)-propan-1,3-dione employed in Step A of Example 24 by an equimolecular quantity of 3-indolylmalondialdehyde and then following substantially the same procedure described in Steps A and B of Example 24.

EXAMPLE 35

6-(4-Pyrimidinyl)-1,8-naphthyridin-2(1H)-one Hydrochloride

This product is prepared by the methods described in Example 34, Steps A-D, employing an equimolecular quantity of pyrimidine-4-acetic acid in place of the indole-3-acetic acid starting material employed in Step A of Example 34.

The products of this invention were found, when tested according to standard protocols in anesthetized dogs to inhibit bronchial constriction induced by one or more bronchoconstrictor agonists; known procedures for evaluating bronchodilating properties of products. In addition, the compounds were also found to exhibit hypotensive properties, probably due to their actions as peripheral vasodilators, and are therefore of potential use as antihypertensive drugs. Intravenous or intraduodenal doses in the range of between about 5 mg./kg. to about 75 mg./kg. provided protection at the $ED_{50}$ level against the induced bronchoconstriction in most animals challenged. Those compounds that also exhibited hypotensive properties were effective within the same dosage range.

The invention further provides pharmaceutical compositions comprising, as active ingredient, at least one of the compounds according to the invention in association with a pharmaceutical carrier or excipient. The product or products may be presented in a form suitable for oral (preferably as capsules, tablets or liquid preparations) or for parenteral administration (in the form of solutions or suspensions) or in aerosols prepared by conventional methods. For example, a capsule can be prepared by conventional methods employing lactose as an excipient and containing per unit dosage 10–25 mg. of active compound. Unit dosages can range between about 5-100 mg. for administration as prescribed by the physician.

While the invention has been illustrated by certain specific members of the novel 1,8-naphthyridine products made by certain specific methods and formulated into certain specific dosage forms, it is to be understood that the invention is not to be considered limited by or to the specific embodiments illustrated but is to encompass other members of the novel products falling within the scope of the generic disclosure and claims as well as other methods or modifications of the methods described for their preparation and other formulations, all of which would be obvious in view of the teaching herein to one skilled in the art.

What is claimed is:

1. A 1,8-naphthyridine-2(1H)-one having the structure:

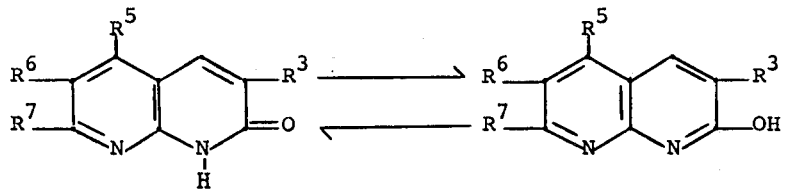

and pharmacologically active salts thereof wherein $R^3$ represents hydrogen, amino, $C_{1-5}$ alkylamino, $(C_{1-5}$ alkyl$)_2$amino, and pyridyl; $R^5$ is phenyl or $R^7$, and $R^7$ represents hydrogen, $C_{1-5}$ alkyl, trifluoromethyl, pentafluoroethyl, chloro- or fluorophenyl, benzyl, naphthyl, pyridyl and thienyl; $R^6$ represents hydrogen, amino, or pyridyl; and wherein at least one of the variables $R^3$ or $R^6$ represents an N-containing substituent as hereinbefore identified provided that when $R^5$, $R^6$ and $R^7$ are hydrogen $R^3$ is other than pyridyl.

2. A product as claimed in claim 1 wherein $R^5$ is phenyl.

3. A product as claimed in claim 1 wherein $R^3$ and $R^6$ are amino.

4. A product as claimed in claim 1 wherein $R^7$ is $C_{1-5}$ alkyl, benzyl, or naphthyl.

5. A product as claimed in claim 1 wherein $R^5$ and $R^7$ each separately represent $C_{1-5}$ alkyl).

6. A product as claimed in claim 1 wherein $R^5$ and $R^7$ each represent methyl.

* * * * *